(12) United States Patent
Shen et al.

(10) Patent No.: US 11,311,649 B2
(45) Date of Patent: Apr. 26, 2022

(54) SILK/PET MIX-WOVEN SCAFFOLD AND PREPARATION METHOD AND USE THEREOF

(71) Applicant: ZHEJIANG UNIVERSITY, Zhejiang (CN)

(72) Inventors: Weiliang Shen, Zhejiang (CN); Hongwei Ouyang, Zhejiang (CN); Xiao Chen, Zhejiang (CN); Jiayun Huang, Zhejiang (CN)

(73) Assignee: ZHEJIANG UNIVERSITY, Zhejiang (CN)

( * ) Notice: Subject to any disclaimer, the term of this patent is extended or adjusted under 35 U.S.C. 154(b) by 0 days.

(21) Appl. No.: 16/899,774

(22) Filed: Jun. 12, 2020

(65) Prior Publication Data

US 2021/0178018 A1  Jun. 17, 2021

(30) Foreign Application Priority Data

Dec. 16, 2019 (CN) .......................... 201911291941.4

(51) Int. Cl.
*A61L 27/18* (2006.01)
*A61L 27/36* (2006.01)
*A61L 27/58* (2006.01)

(52) U.S. Cl.
CPC .......... *A61L 27/3604* (2013.01); *A61L 27/18* (2013.01); *A61L 27/3662* (2013.01); *A61L 27/58* (2013.01); *A61L 2430/10* (2013.01)

(58) Field of Classification Search
CPC .. A61L 27/3604; A61L 27/18; A61L 27/3662; A61L 27/58; A61L 2430/10
See application file for complete search history.

(56) References Cited

U.S. PATENT DOCUMENTS 3,896,500 A * 7/1975 Rambert

FOREIGN PATENT DOCUMENTS

CN  109758262 A  5/2019

OTHER PUBLICATIONS

Chen et al. (Artificial Organs, Published Nov. 9, 2018, pp. 94-108) (Year: 2018).*

* cited by examiner

*Primary Examiner* — Alma Pipic
(74) *Attorney, Agent, or Firm* — Cooper Legal Group, LLC

(57) ABSTRACT

The present invention relates to the technical field of silk scaffolds, and in particular, to a silk/pet mix-woven scaffold and a preparation method and use thereof. The silk/PET mix-woven scaffold is formed by weaving silk and PET fibers. Sericin of the silk is removed. The silk and the PET fibers are mixed and knitted. The PET fibers provide reliable fixation in an early stage to maintain the stability of mechanical properties, and the silk degrades gradually in a later stage to promote the growth of new tissues to achieve the integration of the scaffold and the body. When the scaffold is used for artificial tendon/ligament recovery, its overall performance is better than that of pure silk or pure PET fiber scaffolds, and the scaffold has excellent clinical transformation potential.

10 Claims, 3 Drawing Sheets

SILK/PET MIX-WOVEN SCAFFOLD AND PREPARATION METHOD AND USE THEREOF

RELATED APPLICATION

This application claims the benefit of priority from Chinese Patent Application No. 201911291941.4, filed on Dec. 16, 2019. The content of the aforementioned application, including any intervening amendments thereto, is incorporated herein by reference in its entirety.

TECHNICAL FIELD

The present invention relates to the technical field of silk scaffolds, and in particular, to a silk/pet mix-woven scaffold and a preparation method and use thereof.

BACKGROUND

With the continuous development of China's economy and the improvement of people's living standards, Chinese people are more willing to frequently participate in physical exercises and competitions, and thus are more likely to have motion system injuries. Among them, tendon/ligament injury is the most common motor system injury. A severe tendon/ligament injury, such as an anterior cruciate ligament rupture, not only significantly affects the motor tissues of a patient, but also induces the formation of osteoarthritis if not treated in time, which greatly affects the life quality of the patient.

At present, the patient with the severe tendon/ligament injury, such as the anterior cruciate ligament rupture, often needs surgical reconstruction. A ligament advanced reinforcement system (LARS) system is currently the most advanced fourth-generation artificial ligament, also the only ligament product approved for clinical use in China. An LARS ligament has excellent mechanical properties and can achieve good early fixation strength. The ligament is stable and reliable after the reconstruction, and active rehabilitation training can be started as soon as possible to shorten the recovery period. It is especially suitable for those with acute injuries who require the restoration of motor functions as soon as possible. However, the main component of the LARS ligament is artificially synthesized polyethylene terephthalate (PET) fibers. It is difficult for the surrounding tissues to grow into the PET ligament for integration. In the long term, the ligament may be broken due to fatigue, which causes repair failure, so that it increases the clinician's concerns about the use effect. As a result, the current clinical indications for the LARS ligament are narrow, and the clinical application is greatly limited. How to improve the long-term treatment effect of the LARS ligament and promote its integration with the surrounding tissues has very important value.

Silk has many advantages of low price, excellent biocompatibility, good mechanical property, etc. Some silk products such as silk sutures have been widely used in clinical practices. However, at present, almost all silk tissue tendons/ligaments are broken before the tissues grow after being buried in the body due to the fact that the mechanical property is lost too quickly, which has little clinical application value.

SUMMARY

The present invention provides a silk/PET mix-woven scaffold and a preparation method and use thereof. The silk and PET fibers are mixed and knitted. The PET fibers provide reliable fixation in an early stage to maintain the stability of mechanical properties, and the silk degrades gradually in a later stage to promote the growth of new tissues to achieve the integration of the scaffold and the body. When the scaffold is used for artificial tendon/ligament recovery, its overall performance is better than that of pure silk or pure PET fiber scaffolds, and the scaffold has excellent clinical transformation potential.

In order to realize the objective of the present invention, the present invention provides the following technical solutions:

The present invention provides a silk/PET mix-woven scaffold composed of silk and PET fibers, and sericin of the silk is removed.

Preferably, the proportion of the PET fibers in the silk/PET mix-woven scaffold is greater than 0 and less than 100%.

Preferably, a linear density of the silk is 40-44 den; and a linear density of the PET fibers is 100-200 den.

Preferably, a diameter of the silk/PET mix-woven scaffold is 0.6-2.0 mm.

The present invention provides a preparation method of the silk/PET mix-woven scaffold according to the above technical solution. The method includes the steps of weaving silk and PET fibers with cords and removing the sericin from the obtained mixed base scaffold to obtain the silk/PET mix-woven scaffold.

Preferably, the sericin can be removed by a method for boiling removal by using a sodium carbonate solution, a method for boiling removal by using a detergent, a method for boiling removal by using boric acid or a direct heating removing method.

The present invention provides the silk/PET mix-woven scaffold according to the above technical solution or the application of the silk/PET mix-woven scaffold prepared by the preparation method according to the above technical solution as a biological scaffold in the preparation of a tendon or ligament repair device.

The present invention provides a silk/PET mix-woven scaffold composed of silk and PET fibers, and sericin of the silk is removed. The silk and the PET fibers are mixed and woven to improve the treatment effect of the repair with a simple PET scaffold. Compared with the autologous or allogeneic tendons widely used in clinical practices currently, the silk/PET mix-woven scaffold can omit the step of autologous tendon removal, simplify the surgical operation, shorten the operation time, eliminate the complications of the donor site and reduce the pains of the patient. Compared with the LARS artificial ligament, the silk/PET mix-woven scaffold can meet the needs of human tendon ligament reconstruction by the early mechanical property. In addition, the silk/PET mix-woven scaffold can well promote tissue growth, significantly accelerate the ligamentization process and improve the long-term effect of tissue engineering ligament repair. Compared with a silk tissue engineering ligament, the silk/PET mix-woven scaffold greatly improves the early repair effect of a tissue engineering scaffold under the condition that the long-term repair effect is guaranteed, and improves the clinical repair potential of the silk tissue engineering ligament.

The silk/PET mix-woven scaffold has good biocompatibility, and both silk fibers and PET fibers have good biocompatibility. In addition, the body can generate new ligament-like tissues to gradually replace the silk and eventually promote the generation of the ligament-like tissues.

The silk/PET mix-woven scaffold has good stability, can be stored and transported at room temperature, and has excellent clinical transformation potential.

Further, the initial mechanical property and the degradation rate in vivo can be accurately controlled by adjusting the proportion of the silk and PET fibers in the silk/PET mix-woven scaffold, and the mechanical property can meet the needs of almost all tendon ligament reconstruction.

DETAILED DESCRIPTION

Figure 1:
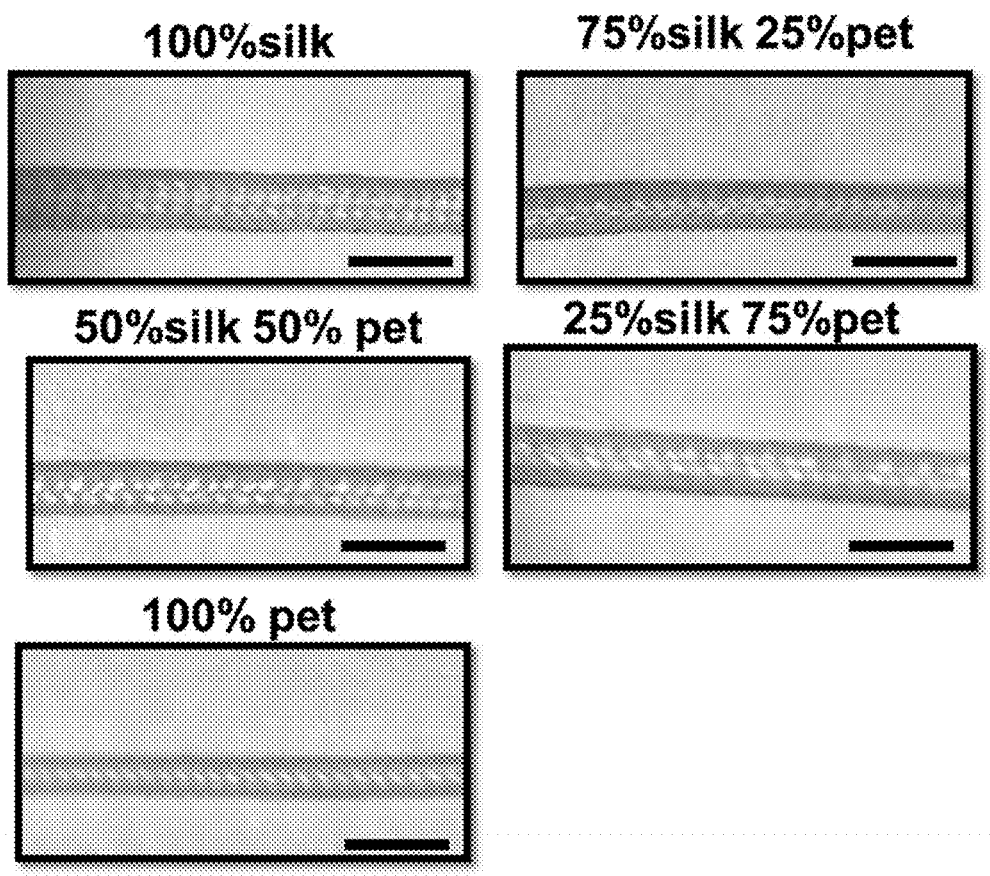
FIG. 1 is a naked eye morphology diagram of five kinds of scaffolds prepared according to the present invention.

The present invention provides a silk/PET mix-woven scaffold composed of silk and PET fibers, and sericin of the silk is removed. The scaffold adopts the silk with the sericin removed, which can significantly improve the biocompatibility of the mix-woven scaffold and greatly reduce the rejection reaction caused by the mix-woven scaffold implanted in the human body.

In the present invention, a linear density of the silk is preferably 40-44 den, more preferably 44 den; the present invention has no special requirements for the specific type of the silk, and any silk well known in the art may be used. In the present invention, a linear density of the PET fibers is preferably 100-200 den, more preferably 100 den. The present invention has no special requirement for the source of the PET fibers, and the market PET fibers well known in the art can be used.

In the present invention, the proportion of the PET fibers in the silk/PET mix-woven scaffold is preferably greater than 0 and less than 100%, more preferably 15-75 wt %, most preferably 50 wt %. The present invention has no special limit on the structure of the silk/PET mix-woven scaffold, and any structure obtained by a weaving method well known in the art may be used. In the present invention, the higher the content of the PET fibers in the mix-woven scaffold, the better the mechanical stability; and the higher the content of the silk, the better the growth of the tissues and the integration of the tissues with the mix-woven scaffold. The initial mechanical property and the degradation rate in vivo can be accurately controlled by adjusting the proportion of the silk and PET fibers in the silk/PET mix-woven scaffold, and the mechanical property can meet the needs of almost all tendon ligament reconstruction.

In the present invention, a diameter of the silk/PET mix-woven scaffold is preferably 0.6-2.0 mm.

The present invention provides a preparation method of the silk/PET mix-woven scaffold according to the above technical solution. The method includes the steps of weaving silk and PET fibers with cords and removing sericin from an obtained mixed base scaffold to obtain a silk/PET mix-woven scaffold.

The silk and PET fibers are subjected to cord weaving to obtain a mixed base scaffold. In the present invention, the cord weaving is preferably performed in a cord weaving machine. The present invention has no special requirement for cord weaving methods, and a weaving method well known in the art can be used. In an embodiment of the present invention, the weaving is performed in a method disclosed by the patent CN 201811637878.0, and the proportion between the silk fibers and the PET fibers is changed by replacing the silk in each bundle of silk with the PET fibers.

After the mixed base scaffold is obtained, the sericin in the mixed base scaffold is removed to obtain the silk/PET mix-woven scaffold. In the present invention, the sericin can be removed by a method for boiling removal by using a sodium carbonate solution, a method for boiling removal by using a detergent, a method for boiling removal by using boric acid or a direct heating removing method.

In the present invention, the method for boiling removal by using a sodium carbonate solution preferably includes immersing a silk base scaffold in a 0.2 M $Na_2CO_3$ aqueous solution (i.e., a degumming solution), boiling for 60-150 minutes, stirring the solution in a stirrer at 200-600 rpm, replacing the degumming solution 2-5 times during the process and drying at 30-80° C. after boiling.

In the present invention, the method for boiling removal by using a detergent preferably includes immersing a silk base scaffold in a 0.2 wt % neutral soap solution (i.e., a degumming solution) at the temperature of 95-100° C., at the same time, stirring the solution in a stirrer at 200-1000 rpm for full degumming, replacing the degumming solution every 20 min for more than 3 times to ensure that the water temperature is greater than 95° C., and drying at 30-80° C. after degumming.

In the present invention, the method for boiling removal by using boric acid preferably includes immersing a silk base scaffold in a 6 wt % boric acid solution (i.e., a degumming solution) at a temperature of 95-100° C., at the same time, stirring the solution in a stirrer at 200-1000 rpm for full degumming, replacing the degumming solution every 20 min more than 3 times to ensure that the water temperature is greater than 95° C., and drying at 30-80° C. after degumming.

In the present invention, the direct heating removing method preferably includes immersing a silk base scaffold in deionized water, heating to 121° C. for 30 min for degumming and drying at 30-80° C. after degumming.

The removal of the sericin from the silk base scaffold can significantly improve the biocompatibility of the mix-woven scaffold and greatly reduce the rejection reaction caused by the mix-woven scaffold implanted in the human body.

The present invention provides the silk/PET mix-woven scaffold according to the above technical solution or the application of the silk/PET mix-woven scaffold prepared by the preparation method according to the above technical solution as a biological scaffold in the preparation of a tendon or ligament repair device. In the present invention, the silk/PET mix-woven scaffold is used for repairing tendons or ligaments as a biological scaffold. The present invention has no special requirement for the implementation of application, and a manner well known to those skilled in the art can be used.

The silk/PET mix-woven scaffold and the preparation method and use thereof as provided by the present invention are described in detail in connection with the following embodiments, but they should not be construed as limiting the claimed scope of the present invention.

Embodiments and Comparative Examples

Different proportions of silk fibers and PET fibers were adopted to perform cord weaving in the high-speed cord knitting machine. In the term of the number, the proportion of the PET fibers was 0%, 25%, 50%, 75% and 100% respectively. A specific weaving method included using 8 bundles of 4-piece silk/PET fiber strands formed by weaving the silk/PET fibers in different proportions (each bundle has 4 fibers, where the number of the PET fibers is 0 (0%), 1 (25%), 2 (50%), 3 (75%) and 4 (100%) respectively) as a scaffold core, adopting 16 bundles of 8-piece silk/PET fibers in different proportions (each bundle has 8 fibers, and the number of the PET fibers is 0 (0%), 2 (25%), 4 (50%), 6 (75%) and 8 (100%) respectively) to knit cladding on the outer portion of the scaffold core, repeating twice to obtain five kinds of base scaffolds in the "core-double-cladding" structure according to the different proportions of the silk and PET fibers; placing the five kinds of base scaffolds in the 0.2M $Na_2CO_3$ solution, boiling for 60 minutes, stirring in the stirrer at 200 rpm, changing water 5 times during the process and drying at 65° C. to obtain a silk scaffold, a silk/PET mix-woven scaffold and a PET fiber scaffold. Except the proportion of the PET fibers, the five kinds of scaffolds are completely same in other parameters including the weaving method. The diameters of the five kinds of obtained scaffolds are sequentially 1.442 mm for 0% PET, 1.148 mm for 25% PET, 1.167 mm for 50% PET, 1.085 mm for 75% PET and 0.9815 mm for 100% PET.

Performance Test

1. The above five kinds of scaffolds are subjected to visual inspection, and the results are shown in FIG. 1. FIG. 1 shows that changing the percentage of the silk/PET fibers slightly affects the initial diameter of the silk/PET mix-woven scaffold.

Figure 2:
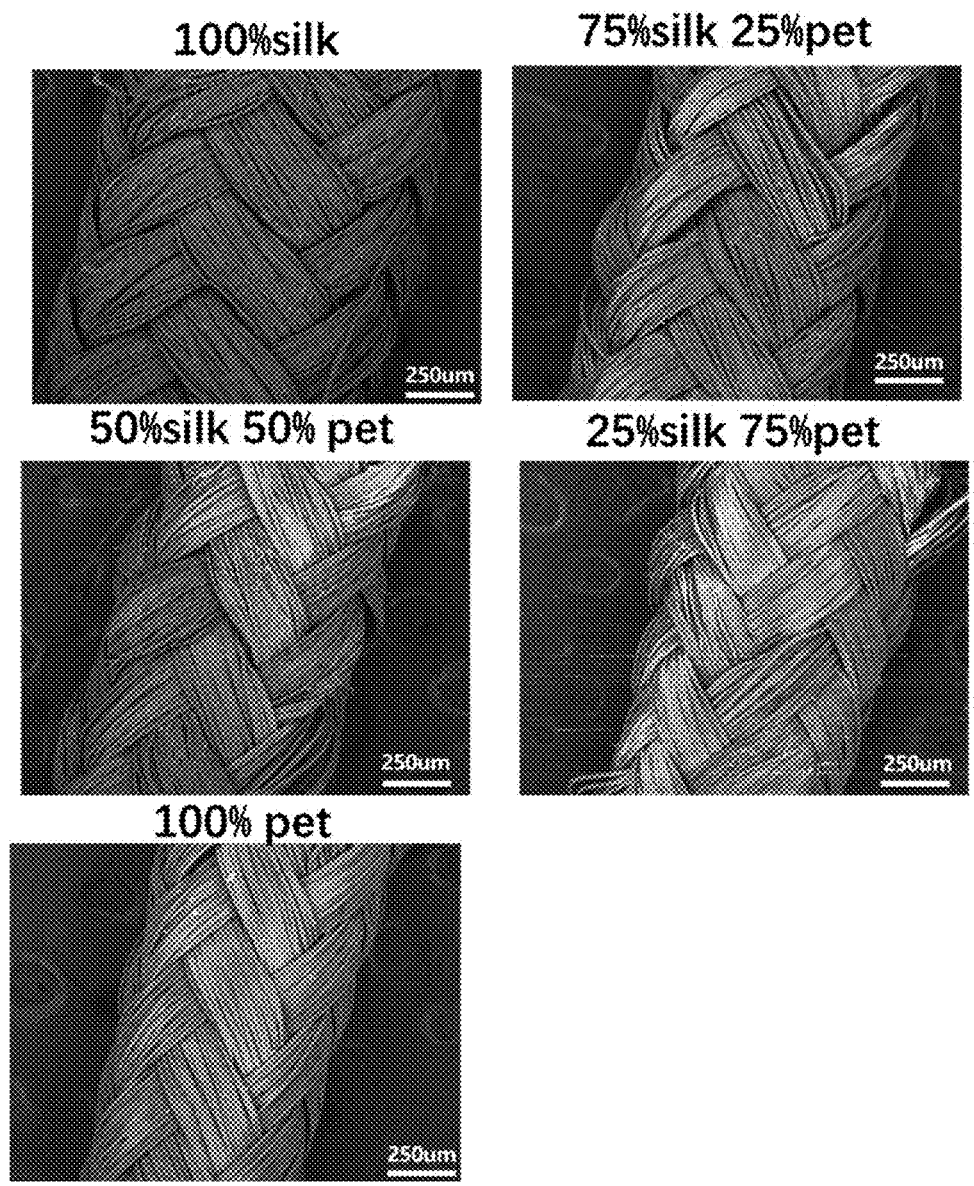
FIG. 2 is a scanning electron microscope diagram of five kinds of scaffolds prepared according to the present invention.

2. The above five kinds of scaffolds are subjected to scanning electron microscope (SEM) observation, and the results are shown in FIG. 2. FIG. 2 shows that all the scaffolds are in an orderly-knitted shape.

3. Characterization of the in vivo mechanical stability and tissue penetration situations of the silk/PET mix-woven scaffold The five different scaffolds were implanted under the skins of rats to simulate the in vivo mechanical loss of the ligaments. The scaffolds were removed from the skin after 4 weeks and 1 year respectively. The mechanical test results are shown in FIG. 3.

Figure 3:
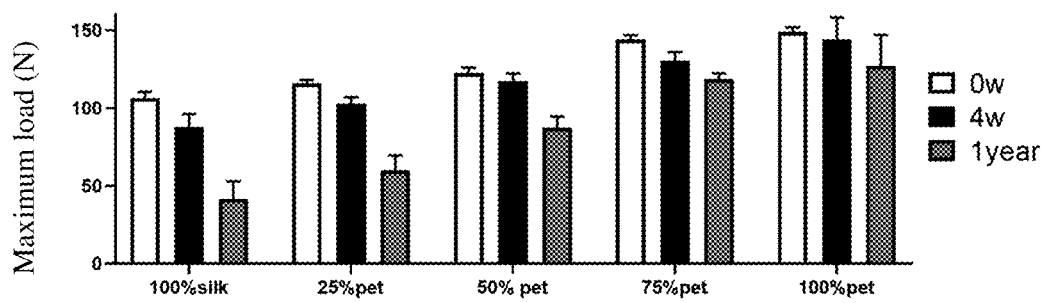
FIG. 3 is a mechanical property diagram of five kinds of scaffolds prepared according to the present invention buried in subcutaneous tissues.

FIG. 3 shows that the mechanical property of the different scaffolds increases with the proportion of the PET fibers, but the initial mechanical property of all the scaffolds is above 100 N, indicating that the initial mechanical property of the scaffolds is excellent. At the same time, FIG. 3 also shows that the pure silk scaffold has faster mechanical reduction after being implanted in the body, and the mechanical loss result is more obvious after 1 year. The scaffolds with the PET fiber percentage greater than 50% have better mechanical stability. The higher the proportion of PET fibers, the better the mechanical stability, indicating that the in vivo mechanical stability of the silk/PET mix-woven scaffold can be affected by changing the proportion of the silk/PET fibers.

Figure 4:
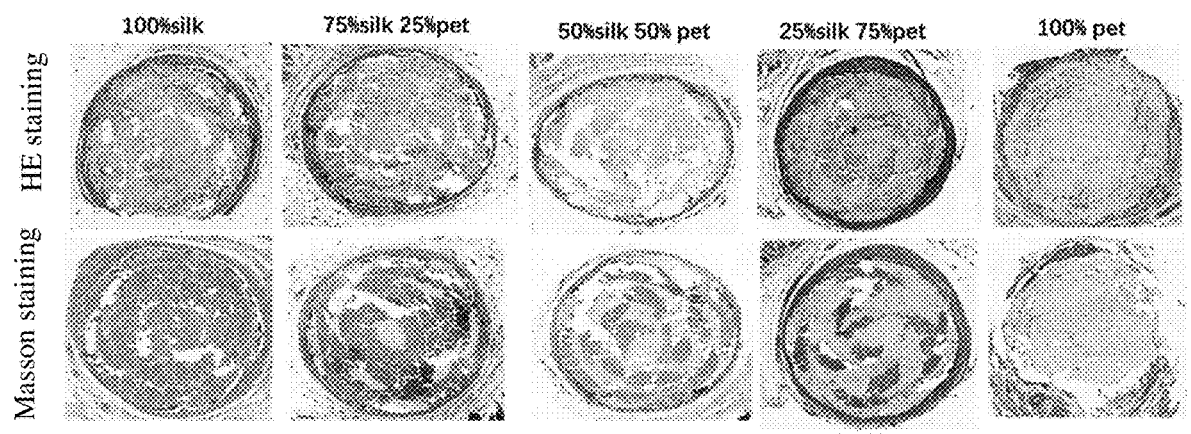
FIG. 4 is a histology diagram of five kinds of scaffolds prepared according to the present invention buried in subcutaneous tissues for 4 weeks.

The subcutaneous tissues of the rats are observed after 4 weeks, and the results are shown in FIG. 4. FIG. 4 shows that there are more tendon-like tissues forming around the scaffolds with the higher proportion of the silk fibers after the scaffolds are implanted in the body. This shows that by the formation of the tendon-like tissues can be promoted by regulating the proportion of the silk fibers and PET.

According to the above embodiments and comparative examples, the present invention provides a silk/PET mix-woven scaffold and a preparation method and use thereof.

The silk and PET fibers are mixed and woven. The PET fibers provide reliable fixation in an early stage to maintain the stability of the mechanical property, and the silk degrades gradually in a later stage to promote the growth of new tissues to achieve the integration of the scaffold and the body. The scaffold is applicable to tendon or ligament repair. When the scaffold is used for artificial tendon/ligament recovery, its overall performance is better than that of pure silk or pure PET fiber scaffolds, and the scaffold has excellent clinical transformation potential.

The foregoing descriptions are only preferred implementation manners of the present invention. It should be noted that for a person of ordinary skill in the art, several improvements and modifications may further be made without departing from the principle of the present invention. These improvements and modifications should also be deemed as falling within the protection scope of the present invention.

What is claimed is:

1. A mix-woven scaffold comprising silk and polyethylene terephthalate (PET), wherein:
   the mix-woven scaffold comprising silk and PET is formed by weaving silk fibers and PET fibers and removing sericin from the silk fibers,
   a linear density of the silk fibers is 40-44 den; and
   a linear density of the PET fibers is 100-200 den.

2. The mix-woven scaffold comprising silk and PET according to claim 1, wherein a diameter of the mix-woven scaffold comprising silk and PET is 0.6-2.0 mm.

3. A preparation method of the mix-woven scaffold comprising silk and PET according to claim 1, comprising the steps of weaving the silk fibers and the PET fibers with cords to form a mixed base scaffold, and removing sericin from the mixed base scaffold to obtain the mix-woven scaffold comprising silk and PET.

4. A preparation method of the mix-woven scaffold comprising silk and PET according to claim 2, comprising the steps of weaving the silk fibers and the PET fibers with cords to form a mixed base scaffold, and removing sericin from the mixed base scaffold to obtain the mix-woven scaffold comprising silk and PET.

5. The preparation method according to claim 3, wherein the step of removing the sericin is selected from the group consisting of boiling the mixed base scaffold in a sodium carbonate solution, boiling the mixed base scaffold in a detergent solution, boiling the mixed base scaffold in a boric acid solution, and heating the mixed base scaffold in deionized water.

6. The preparation method according to claim 4, wherein the step of removing the sericin is selected from the group consisting of boiling the mixed base scaffold in a sodium carbonate solution, boiling the mixed base scaffold in a detergent solution, boiling the mixed base scaffold in a boric acid solution, and heating the mixed base scaffold in deionized water.

7. A repair device comprising a biological scaffold comprising the mix-woven scaffold comprising silk and PET according to claim 1, wherein the repair device is for a tendon or a ligament.

8. A repair device comprising a biological scaffold comprising the mix-woven scaffold comprising silk and PET according to claim 2, wherein the repair device is for a tendon or a ligament.

9. A repair device comprising a biological scaffold comprising the mixed-woven scaffold comprising silk and PET obtained by the preparation method according to claim 3, wherein the repair device is for a tendon or a ligament.

10. A repair device comprising a biological scaffold comprising the mixed-woven scaffold comprising silk and PET obtained by the preparation method according to claim 5, wherein the repair device is for a tendon or a ligament.

\* \* \* \* \*